United States Patent [19]

Hobbs

[11] 4,439,627

[45] Mar. 27, 1984

[54] CATALYST AND REVERSE DISPROPORTIONATION PROCESS

[75] Inventor: Charles F. Hobbs, Des Peres, Mo.

[73] Assignee: Monsanto Company, St. Louis, Mo.

[21] Appl. No.: 403,257

[22] Filed: Jul. 29, 1982

[51] Int. Cl.³ ............................................... C07C 5/09
[52] U.S. Cl. .................................... 585/435; 585/646
[58] Field of Search ................................ 585/435, 646

[56] References Cited

U.S. PATENT DOCUMENTS

| 3,300,007 | 11/1981 | Polyakov et al. | 585/323 |
| 3,658,930 | 4/1972 | Kenton et al. | 585/364 |
| 3,728,414 | 4/1973 | Van Helden et al. | 585/646 |
| 3,764,635 | 10/1973 | Fattore et al. | 585/643 |
| 3,792,107 | 2/1974 | Fattore et al. | 585/646 |
| 3,965,206 | 6/1976 | Montgomery et al. | 585/319 |
| 4,144,197 | 3/1979 | Riesser et al. | 252/462 |
| 4,192,961 | 3/1980 | Polyakov et al. | 585/319 |

FOREIGN PATENT DOCUMENTS

| 7111822 | 5/1972 | Netherlands | 585/435 |
| 1205677 | 9/1970 | United Kingdom . | |

Primary Examiner—Curtis R. Davis

[57] ABSTRACT

A catalyst containing tungsten, an alkali or alkaline earth component, and iron on a support, preferably silica gel, is disclosed which is useful in reverse disproportionation of stilbene and ethylene to produce styrene.

12 Claims, No Drawings

CATALYST AND REVERSE DISPROPORTIONATION PROCESS

BACKGROUND OF THE INVENTION

1. Field of the Invention

The present invention relates to a catalyst and a process for reverse disproportionation of ethylene and stilbene to produce styrene. The catalyst comprises tungsten, potassium, and iron on a silica support.

2. Description of the Prior Art

The production of styrene from stilbene and ethylene is disclosed in U.S. Pat. No. 3,965,206, the teachings of which are incorporated by reference. Use of conventional disproportionation catalysts such as cobalt molybdate on alumina, or tungsten oxide or silica, alumina or silica-alumina, for reverse disproportionation is taught.

U.S. Pat. No. 3,764,635, Fattore, et al, the teachings of which are incorporated by reference, teaches a process for disproportionating olefins using a catalyst of tungsten and bismuth on a support, preferably silica. The catalyst is active for disproportionation without any activation step.

U.S. Pat. No. 3,792,107, Fattore, et al, the teachings of which are incorporated by reference, discloses use of a catalyst of tungsten and copper or tungsten and Group VIII metals, preferably Fe, Co, or Ni, or silica or other support. It is claimed that this catalyst requires no activation before use in disproportionation.

U.S. Pat. No. 3,728,414, Helden, et al, the teachings of which are incorporated by reference, teaches a conventional olefin disproportionation catalyst with a promoter, a Group IIIa metal on an alumina carrier. Conventional olefin disproportionation catalysts are said to contain titanium, vanadium, chromium, manganese, zirconium, niobium, molybdenum, technetium, ruthenium, rhodium, palladium, tin, hafnium, tantalum, tungsten, rhenium, osmium, and iridium. This reference teaches that additional components, e.g., coactivators, hydrogenating components, components for isomerization of the double bond, and the like may also be added. Coactivators listed include cobalt oxide, and compounds of iron, nickel, and bismuth.

U.S. Pat. No. 4,192,961 teaches conversion of a mixture of dibenzyl and stilbene with ethylene in the presence of a catalyst of chromium oxide, tungsten oxide, an oxide of an alkali metal and silica or alumi-silicate. Styrene yields of 78 to 80 wt %, based upon conversion of ethylbenzene, dibenzyl and stilbene, are claimed.

U.S. Pat. No. 3,658,930, Kenton, et al, the teachings of which are incorporated by reference, teaches disproportionation of olefins using a rhodium oxide promoter on conventional olefin disproportionation catalyst, e.g., tungsten, molybdenum, rhenium, or tellurium on silica.

U.K. Patent specification No. 1,205,677 teaches disproportionation of olefins using a conventional catalyst, such as molybdenum trioxide, tungsten trioxide or rhenium heptoxide on alumina, silica, or alumina-silica, and incorporating into this conventional catalyst a second component to effect double bond isomerization of olefins. Group VIII noble metals are suggested as being suitble, with preferred isomerization catalysts containing platinum and especially palladium. An alkali or alkaline earth metal ions are added to the catalyst to serve as a base to inhibit the oligomerization of branched chain olefins.

None of these prior art catalysts are believed to possess sufficient activity and stability to permit their use in a commercial reverse disproportionation process.

Although it is desirable to have a catalyst which can be successfully reactivated at approximately the same temperature used for the reverse disproportionation reaction, the choice of a commercial catalyst must depend on other factors as well. A very significant factor is the cost of the catalyst. Same promoters, such as noble metals, are expensive.

Sometimes the increased productivity of a catalyst, which requires a high temperature activation more than justifies the increased costs associated with wear and tear on equipment and catalyst due to swings in temperature. Similarly, a longer cycle length, between regenerations is important in a commercial unit.

Use of iron, as a catalyst additive, significantly increases the ability of the catalyst to effect the reverse disproportionation reaction for extended periods of time, the iron slightly reduces productivity during the start of a run, but at the end of a 12-hour run the iron-promoted catalyst has a higher productivity than standard catalyst.

SUMMARY OF THE INVENTION

The present invention provides a catalyst comprising catalytically effective amounts of iron, tungsten, and an alkali or alkaline earth component on a carrier material.

In another embodiment, the present invention provides a process for the reverse disproportionation of stilbene and ethylene which comprises contacting stilbene and ethylene at reverse disproportionation conditions with an activated catalyst containing iron, tungsten, and an alkali or alkaline earth component or compounds thereof supported on a carrier material, to produce styrene.

In a more limited embodiment, the present invention provides a process for the reverse disproportionation of stilbene and ethylene into styrene comprising contacting the stilbene and ethylene at temperature of 300 to 600 C. with an activated catalyst comprising tungsten, iron, and an alkali or alkaline earth metal or compounds thereof on silica gel carrier, and wherein the atomic ratio of iron to tungsten is from 1:20 to 2:1, to produce styrene, and continuing said contact until said catalyst has been at least partially deactivated by coke deposition, removing said deactivated catalyst from contact with reactants and regenerating said catalyst by oxidizing coke from said catalyst with an oxygen containing gas to produce an oxidized catalyst with reduced coke content and thereafter activating said catalyst by contacting said oxidized catalyst with activating gas at 400 to 600 C. for a time sufficient to activate said catalyst, and thereafter returning said catalyst to contact with stilbene and ethylene for further reverse disproportionation of stilbene and ethylene into styrene.

DETAILED DESCRIPTION

The Reverse Disproportionation Reaction

The total reaction of this invention may be represented by the following equation:

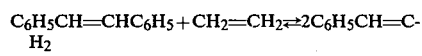

Catalyst

The catalyst may contain from 0.1 to 10 wt % W, preferably 1 to 6 wt %, and 0.005 to 5 wt % Fe, preferably 0.05 to 2 wt %. The catalyst also has 0.01 to 2%, preferably 0.03 to 0.3 wt % alkali or alkaline earth metal ion, preferably potassium. Other promoters may be present.

The support is preferably silica gel, but any other support used for conventional disproportionation catalysts may also be used, though the catalyst performance may change some.

Reaction Conditions

The reverse disproportionation reaction conditions are given in U.S. Pat. No. 3,965,206, this teachings of which are incorporated by reference. In general, temperatures of 300 to 600 C. are adequate. Pressures from subatmospheric to 1000 atm. absolute are suitable, but operation at 1 to 10 atmospheres gives good results.

Hydrogen or nitrogen or inerts may be present during the disproportionation reaction. Nitrogen is believed inert. Adding hydrogen may, or may not, cut down on catalyst coking, and may overreduce the catalyst. Nitrogen, and hydrogen and other inert gases will also cut down residence time of reactants in the reactors, if desired. I prefer to operate with the reactants as the sole feed to the reactor. The feed to the process of the present invention consists of relatively pure stilbene and ethylene. Other materials may be present, but polar materials act as catalyst poisons.

EXAMPLES

Reactor

The experimental apparatus used in all examples consisted of a 0.5-inch OD stainless steel tube, 18–31 cm long. The catalyst was maintained in the reactor as a fixed bed. Reactants flowed in a vapor phase, down flow, through the catalyst bed. The catalyst was supported on a quartz wool plug resting on an inert support. During the early phases of the study, ⅛-inch alundum beads were used, but experiments showed that this material was not inert and caused some coking. The later studies were conducted using ⅛-inch long quartz billets cut from 2 mm rod as a support.

Special precautions were taken to exclude oxygen from the apparatus and to keep the stilbene feed in the vapor phase. Special steam tracing, heating, and nitrogen purging of lines contacting stilbene are essential in a pilot plant, but may not be as critical in a large scale commercial plant.

Catalyst Preparation

A series of catalysts was prepared. The basic catalyst contained 0.56 wt % $WO_3$ and 0.038 wt % $K_2O$. The catalyst was prepared by adding 20 g of 14–35 mesh Davison Grade 59 silica gel, which had been freshly calcined, to 28 ml of a solution containing 5 ml of 0.0236N KOAc solution, 10 ml of $H_2O$ and 13 ml of concentrated $NH_4OH$. The silica gel was only minimally wetted by the 28 ml of liquid. The mixture was shaken for 30 minutes, then dried overnight in a stream of air on a filter, and finally calcined for 2 hours at 600 C. Various additives, those which were soluble in the alkaline solution described above, were simply added to the alkaline solution along with the potassium and tungsten components. In some cases, because of solubility limitations, ammonium hydroxide would not dissolve the additive, so in these cases a few drops of concentrated $HNO_3$ was added to obtain a clear solution. In all cases the total liquid volume of impregnating solution was 28 ml, the exact volume was obtained by adjusting the amount of water added. In all cases, except where noted, additives were added sufficient to give an atomic ratio of tungsten: additive of 5:1. I believe the additives, the added metallic components, were present as oxides on the catalysts, because of the calcination in air for two hours at 600 C.

When rhodium was added, a different procedure was used as no water soluble rhodium compound was readily available. A large batch of base catalyst (containing 0.56 wt % $WO_3$ and 0.038 wt % $K_2O$) was made up as described above. A 20.12 g portion of this catalyst was then impregnated with 25 ml of a methanol solution containing 0.0375 g of Rh (acac). This alcoholic impregnating solution was sufficient to just impart wetness to the catalyst. After shaking for 30 minutes, drying in air, and calcining for 2 hours at 600 C. the catalysts were ready for use.

Table I shows a listing of catalysts prepared.

TABLE I

PREPARATION OF 0.56% $WO_3$, 0.038% $K_2O$ CATALYSTS WITH ADDED METALLIC COMPONENTS

| Additive | Compound Used | Wt. of Compound[a], g. | Comments |
|---|---|---|---|
| Pt | $Pt(NH_3)_2(ONO)_2$ | 0.0330[b] | |
| Pd | $Pd(NH_3)_2(ONO)_2$ | 0.0232 | 5 drops $HNO_3$, boiled to dissolve salts |
| Ni | $Ni(NO_3)_3.6H_2O$ | 0.0281 | No $NH_4OH$ |
| Zn | $Zn(OAc)_2.2H_2O$ | 0.0212 | No $NH_4OH$; 5 drops 30% $H_2O_2$ |
| Cr | $Cr(NO_3)_3.9H_2O$ | 0.0387 | No $NH_4OH$; 5 drops 30% $H_2O_2$ |
| Fe | $Fe(NO_3)_3.9H_2O$ | 0.0390 | No $NH_4OH$; 5 drops 30% $H_2O_2$; 10 drops $HNO_3$ |
| Ru | $RuNO(NO_3)_3$ | 0.0306[c] | 5 drops 30% $H_2O_2$ |
| Mo | $(NH_4)_6Mo_7O_{24}.4H_2O$ | 0.0171 | |
| V | $NH_4VO_3$ | 0.0114[d] | |
| Sn | $SnSO_4$ | 0.0218 | No $NH_4OH$; 10 drops conc. $H_2SO_4$, 4 drops $HNO_3$ |
| Re | $Re_2O_7.3$ (Dioxane) | 0.0362 | NO $NH_4OH$; 5 drops 30% $H_2O_2$ |
| Ag | $AgNO_3$ | 0.0164 | |
| Ce | $Ce(NO_3)_3.6H_2O$ | 0.0419 | No $NH_4OH$ |
| Eu | $Eu(NO_3)_3.6H_2O$ | 0.0431 | No $NH_4OH$ |
| As | $As_2O_5.NH_2O$ | 0.0127[e] | No $NH_4OH$ |
| U | $UO_2(C_2H_3O_2)_2.2H_2O$ | 0.0410 | No $NH_4OH$ |
| Mn | $Mn(C_2H_3O_2)_2.4H_2O$ | 0.0237 | No $NH_4OH$ |

TABLE I-continued

PREPARATION OF 0.56% WO₃, 0.038% K₂O CATALYSTS WITH ADDED METALLIC COMPONENTS

| Additive | Compound Used | Wt. of Compound[a], g. | Comments |
|---|---|---|---|
| Rh | Rh(acac) | 0.0375 | Alcoholic impregnation. |

[a]20 g of silica gel base
[b]61.00% Pt
[c]35.87% Ru
[d]76.90% $V_2O_5$
[e]87.65% $As_2O_5$

Catalyst Activation

Catalysts were activated, in situ, by passing 200 scc/min of CO over the catalyst at a specified temperature for specified time. It is possible to use other activating gases, or no gas at all, but a CO activation procedure was chosen as a standard one to permit screening of the effects of various additives on catalyst activation.

Test Procedure

The activated catalyst was then tested for its activity on a standard feed consisting of 200 scc/min ethylene and 40 scc/min of stilbene. The residence time in the catalyst bed was 0.3 seconds. The products were analyzed by gas chromatography.

After the catalyst lost activity, it was regenerated by contacting it with 48 scc/min of air for 45 minutes at 575 C.

A typical operating sequence is presented below:

A. Activation Cycle 1. 25 min. Nitrogen purge of lines and reactor system (200 cc/min.). Ethylene purge of line up to oxygen trap. Reactor temperature equilibrated to activation temperature.
2. 5 min. Nitrogen purge continuing. Ethylene purge of lines through oxygen trap to vent, located at ethylene-to-saturator feed valve. CO flow to vent to purge CO line in panel control board.
3. 55 min., typical. Nitrogen off. CO feed to reactor for activation, feed rate typically 200 cc/min. Ethylene purge to vent continuing, with oxygen meter (Teledyne Trace Oxygen Analyzer Model 311-1) connected to vent to monitor ethylene quality.
4. 5 min. Nitrogen purge to vent to clear lines in control panel. CO feed to reactor and ethylene feed to vent continuing.
5. 15 min. Nitrogen purge of reactor and lines. Ethylene feed to vent continuing. Temperature changed to disproportionation run temperature.
6. 5 min. Ethylene feed to reactor, bypassing saturator. Saturator feed valve open to reactor to equalize pressure.

B. Disproportionation Cycle 1. 30 min. Ethylene feed through stilbene saturator and thence to reactor; GC sampling progam called during last 60 sec. of cycle. Step is repeated as desired.

C. Burn-off Cycle 1. 5 min. Nitrogen purged to vent to clear lines in control panel. Ethylene feed to saturator off, but saturator feed valve to reactor open to equalize pressure.
2. 60 min. Nitrogen purge to reactor (48 cc/min). Temperature changed to burn-off temperature, usually 575 C. Air purged to vent to equilibrate pressure in line.
3. 45 min. Air feed to reactor, 48 cc/min. GC analysis for $CO_2$ called.
4. 15 min. Nitrogen purge, 200 cc/min., through reactor system.
5. Shut down or recycle.

This procedure was used to test the different catalyst formulations. Experimental results are shown as productivity, measured as moles of styrene per liter of catalyst per hour. 34 moles per liter per hour represents about 83% conversion of stilbene to styrene. Productivity is reported both for the start of run conditions (initial) and at the end of the run, i.e., after 4.5 hours of operation (final). The data are presented below in Table IIA.

TABLE IIA

EFFECT OF ADDITIVES ON CATALYST ACTIVATION

| Catalyst[a] Additive | Activation Conditions | | Productivity[b] | |
|---|---|---|---|---|
| | Time | Temp. | Initial | Final |
| None (STD) | | None | 4.19 | 6.74 |
| | 1 hr | 450 | 8.05 | 12.65 |
| | 8 hr | 450 | 27.65 | 19.43 |
| Ce | 1 hr | 450 | 8.13 | 12.30 |
| Eu | | None | 4.01 | 6.27 |
| | 1 hr | 450 | 6.91 | 12.57 |
| As | | None | 2.16 | 3.99 |
| | 1 hr | 450 | 8.62 | 12.91 |
| | 1hr | 450 | 8.92 | 13.31 |
| Fe | 1 hr | 450 | 9.07 | 17.79 |
| Cr | 1 hr | 450 | 7.10 | 12.20 |
| Ni | 1 hr | 450 | 7.51 | 13.82 |
| Ru | 1 hr | 450 | 4.68 | 11.19 |
| Pt | 1 hr | 450 | 9.38[c] | 7.21[c] |
| Pd | 1 hr | 450 | 7.29[c] | 6.35[c] |

[a]All additives at 5:1 W:additive mole ratio unless otherwise noted.
[b]All runs were for 4.5 hr. Run temp., 425 C.
[c]Average for 2 runs.

The test apparatus was then partially dismantled and rebuilt. A number of additional tests were then run. The main difference between operations reported in Table IIA and Table IIB, presented hereafter, is the amount of oxygen contamination. I believe that the data presented in IIA reflect less oxygen contamination than those in Table IIB. Since the testing occurred under superatmospheric pressure, it was thought that there would be no air contamination due to leaks in the piping. Reactants might leak out, but air would not get in. Several ppm oxygen diffused into the test apparatus through a leak to increase the oxygen level, and decrease the catalyst activity. Oxygen is a catalyst poison. The amount of $O_2$ contamination was relatively constant during the IIA testing period, I estimate about 0.2 ppm $O_2$ by volume. For the IIB testing period about 0.3 ppm $O_2$ by volume was present. I checked the activity of my standard, or reference, catalyst periodically during the IIA and IIB testing periods. The standard, or reference, catalyst consistently gave lower productivity during the IIB tests. The results of the more $O_2$-contaminated runs are reported in Table IIB. All tests were conducted at about 3 psig, or 1.2 atm, absolute.

TABLE IIB

EFFECT OF ADDITIVES ON CATALYST ACTIVATION

| Catalyst[a] Additive | Activation Conditions | | Productivity | |
|---|---|---|---|---|
| | Time | Temp. | Initial | Final |
| None (STD) | 1 hr | 450 | 6.09 | 11.04 |
| | 1 hr | 450 | 5.87 | 11.49 |
| | 1 hr | 450 | 4.53 | 9.63 |
| Rh | 1 hr | 450 | 9.82 | 10.60 |
| | 1 hr | 450 | 2.98 | 8.16 |
| | 1 hr | 450 | 2.41 | 7.45 |
| | 8 hr | 450 | 2.76 | 6.53 |
| Mo | 1 hr | 450 | 3.92 | 7.75 |
| | 1 hr | 450 | 4.75 | 7.56 |
| V | 1 hr | 450 | 1.05 | 2.86 |
| Sn | 1 hr | 450 | 0.04 | (0.18) |
| | 1 hr | 450 | 1.34 | (1.61) |
| Re | 1 hr | 450 | 4.49 | 4.26 |
| Zn | 1 hr | 450 | 2.82 | 4.32 |
| Ag | 1 hr | 450 | 3.42 | 8.02 |
| | 1 hr | 450 | 4.32 | 8.48 |
| U | 1 hr | 450 | 4.98 | 5.47 |
| Mn | 1 hr | 450 | 3.76 | 4.04 |

[a]All additives at 5:1 W:additive mole ratio unless otherwise noted.

It is believed that results can be compared very well within Table IIA, or within Table IIB. Direct comparison of an additive listed in Table IIB with an additive from the Table IIA is harder to make, because of the increased oxygen contamination in those runs presented in Table IIB. It is believed that the relative activities, i.e., activity of a catalyst in Table IIB with an additive compared to activity of a catalyst with no additives from Table IIB can be compared. These data, relative activation, for initial activity, are reported in Table III. The relative activities are probably more significant than relative end of run activities, so comparisons were made based on initial activity. A single number means the catalyst was stable after repeated regenerations, multiple numbers means activity declined.

TABLE III

| Additive | Relative Activities |
|---|---|
| Fe | 1.13 |
| As | 1.10 |
| Pt | 1.09 |
| Ce | 1.01 |
| Rh | 1.01, 0.56, 0.45 |
| U | 1.03 |
| None (Standard) | 1.00 |
| Re | 0.93 |
| Ag | 0.89, 0.71 |
| Mo | 0.89, 0.74 |
| Ni | 0.93, 0.77 |
| Cr | 0.88 |
| Eu | 0.86 |
| Pd | 0.85 |
| Mn | 0.78 |
| Zn | 0.58 |
| Ru | 0.58 |
| Sn | 0.31 |
| V | 0.16, 0.17, 0.20, 0.20 |

From these data, it is apparent that a reverse disproportionation catalyst containing iron is more active than the reference catalyst. These results were obtained with a relatively mild activation, 450 C. This relatively low temperature was picked because the reverse disproportionation reaction runs at 450 C. I decided to conduct further tests to see what effect a higher temperature activation step had on catalyst activity and life. Catalyst life may be a very significant factor because the presence of polars, such as oxygen, hurts catalyst activity.

Oxygen is a reversible but strong catalyst poison. I tried to eliminate as much oxygen as I could from my test apparatus; however, the lowest oxygen level consistently obtainable was 0.3 ppm at this point in the testing program. This $O_2$ level was estimated from measurements made at the reactor outlet using the Teledyne Trace Oxygen Analyzer.

Oxygen contamination is a very serious problem in a pilot plant because the sizes of the feed streams are relatively small compared to the leaks that may be present in the plant. This may not be as much of a problem in a commercial unit, however, it may be a significant problem commercially if it is not possible to remove sufficient oxygen or polars from the feed.

To accomodate this eventuality, or to design a process for use in reverse disproportionation of feed streams which contain significant amounts of oxygen contamination, or other polar contaminants, I tried to find a catalyst which would withstand relatively more catalyst poisons than could the prior art systems.

In this series of tests, a slightly different activation procedure was used, all catalysts were activated at 575 C. for one hour. This is a much more severe activation step than the 450 C., one hour activation used in most of my prior work. The reason for using the higher activation temperature was to give the catalyst maximum activity. In the prior tests, using the 450 C. activation, the purpose of the experiments was to find a catalyst which could be sufficiently activated at a temperature near that of the reverse disproportionation reactor.

Under the conditions of the reactor flow described above, the feed to the reactor zone contained about 0.3 ppm volume of oxygen. Results of these experiments are reported to the Tables IVA, B, and C.

TABLE IVA

EFFECT OF ADDITIVES WITH HIGH TEMPERATURE ACTIVATION

| Catalyst[a] Additive | Productivity[b] | | Coke %, Cat |
|---|---|---|---|
| | Initial | Final | |
| Fe | 32.40 | 29.42 | 0.25 |
| None (STD) | 33.73 | 26.48 | 0.43 |
| Pt | 32.90 | 22.47 | 0.37 |
| Ce | 32.87 | 25.29 | 0.25 |
| As | 31.52 | 25.14 | 0.24 |
| Ru | 30.94 | 26.95 | 0.23 |
| Cr | 28.86 | 22.61 | 0.35 |
| Ni | 21.68 | 24.89 | 0.16 |
| | 21.77 | 24.01 | 0.25 |
| Eu | 30.43 | 20.93 | 0.27 |

TABLE IVB

| Catalyst Additive | Productivity | | Coke %, Cat |
|---|---|---|---|
| | Initial | Final | |
| None (STD) | 33.53 | 25.86 | 0.06 |
| V | 11.47 | 7.78 | — |
| Mo | 15.88 | 10.24 | — |
| Sn | 16.3 | — | — |
| Re | 30.85 | 9.46 | 0.19 |
| Zn | 12.44 | 10.13 | 0.15 |

TABLE IVC

| Catalyst Additive | Productivity Initial | Productivity Final | Coke %, Cat |
|---|---|---|---|
| None (STD) | 30.91 | 13.20 | — |
| | 28.94 | 12.49 | — |
| Ag | 28.62 | 13.11 | 0.13 |
| U | 27.09 | 10.42 | 0.06 |
| Mn | 20.02 | 7.84 | 0.09 |

[a] All additives at 5:1 W:additive mole ratio unless otherwise noted.
[b] Run for 12 hrs, Run Temp, 425 C; Feed Rate, 200 scc/min ethylene. 40 scc/min SB. Res. Time, 0.3 sec.
Activation, 1 hr at 575 C.
Productivities in moles of Sm/L/hr; a productivity of 34 m/l/hr. ≈83% conversion.

As was previously discussed, data should only be compared within each table, as it is believed that oxygen levels increased somewhat between the data presented in Tables IVA, IVB, and IVC. Data in Table IVA and Table IVB represent operation with about 0.3 ppm volume oxygen. Data from Table IVC represent an oxygen level of about 0.5 ppm volume oxygen. Although the Fe-promoted catalyst had a slightly lower initial activity than the reference catalyst, the iron-promoted catalyst had a final productivity of 29.42 after 12 hours, compared to the reference catalyst with a productivity of 26.48.

The iron-promoted catalyst also had a relatively low coke on catalyst level at the end of the 12 hour run, 0.25 wt % coke on catalyst as compared to 0.43 wt % coke on the reference catalyst. Because of small sample sizes and difficulties encountered in reproducing other coke numbers. I do not have as much confidence in the reported coke levels as I do on the reported productivity levels, however, the reduced coke level is consistent with increased activity. Somewhat contradictorily, a number of other catalysts had poor initial and final productivities and yet also had relatively low coke levels on the catalyst.

Also of interest, the iron-promoted catalyst does not show its outstanding productivity when subjected to relatively mild activation. Comparing catalysts promoted with Fe with the standard catalyst using a 450 C. activation for 1 hour with CO gas, showed some improvement of initial activity, with significantly enhanced activity later on, although none of the activities of either the standard catalyst or the iron catalyst are considered sufficiently high to be viable commercial catalysts. The superiority of the iron-promoted catalyst over conventional catalysts becomes apparent with the more severe activation step.

I am not sure what the optimum amount of iron is. I know a 1:5 Fe:W atomic ratio gives good results.

I believe that good results can be obtained with Fe:W atomic ratios of 1:20 to 2:1 and preferably 1:10 to 1:3.

If I were designing a commerical plant today, I would conduct further experiments to see if the various catalytic components could be optimized further.

I would probably use a catalyst containing 2 to 10 times as much metal content as those catalysts used in the experiments. Commercially you want more active catalysts, and smaller reaction vessels, and would use catalysts with a higher metal loading. I used very lightly loaded catalysts for my experiments because the catalyst was extremely active. "Full strength" catalyst established equilibrium conditions so rapidly that I could not discern relatively smaller differences caused by different additives. Based on other experimental work, metal loadings ten times as high as probably be achieved using similar impregnation procedures, with five or tenfold increase in activity. Phrased another way, the reactants see the active metals, not the support, and the amount of conversion per gram of catalytic components (excluding support) is roughly constant. More metal on the support should provide more resistance to poisoning by trace amounts of $O_2$ and polars.

I would like to learn more about the active form of the catalysts I tested. The active form may be a simple oxide or may be a mixed heteropolyacid of $SiO_2$, $WO_3$ and $MO_x$, where M is the additive metal. It is possible that the oxides mentioned and claimed do not exist as discrete oxides, but instead form some complex polymeric structure.

Commercially, I would operate the plant with whatever oxygen stripping columns or oxygen and water absorbers were necessary to ensure oxygen, and other contaminants, especially polar ones, were excluded from the plant.

My catalyst can be disposed within the reactor as a fixed bed, fluidized bed, moving bed, ebullating bed, or any other reactor configuration. The advantage of the fluidized, moving and ebullated bed reactors is that catalyst addition and withdrawal can be performed continuously. Thus, coke, or carbon deposition on the catalyt can be burned off, the catalyst activated, and returned to the reactor without shutting down the reactor. The disadvantage of this mode of operation is that the reactor designs are fairly complicated, as compared to simple fixed-bed down-flow design. When fixed-bed reactors are used, preferably, two or three reactors are provided in parallel, permitting one or more reactors to be taken off stream for carbon burn-off and activation while the other reactor(s) remain on stream.

What is claimed is:

1. A process for the reverse disproportionation of stilbene and ethylene which comprises contacting stilbene and ethylene at reverse disproportionation conditions with an activated catalyst containing catalytically effective amounts of iron, tungsten, and an alkali or alkaline earth component or compounds thereof supported on a carrier material, to produce styrene.

2. Process of claim 1 wherein the carrier material is silica gel.

3. Process of claim 1 wherein the alkali or alkaline earth component is potassium.

4. Process of claim 1 wherein the catalyst contains 0.1 to 10 Wt. % W, 0.01 to 2 wt % alkali or alkaline earth component and 0.005 to 5 wt % Fe.

5. Process of claim 1 wherein the catalyst contains 1 to 6 wt % W, as $WO_3$, 0.05 to 2 wt % Fe as $Fe_2O_3$ and 0.03 to 0.3 wt % K as $K_2O$ and the catalyst support is silica gel.

6. Process of claim 1 wherein the iron to tungsten ratio is 1:20 to 2:1.

7. Process of claim 1 wherein the iron to tungsten ratio is 1:5.

8. A process for the reverse disproportionation of stilbene and ethylene into styrene comprising contacting the stilbene and ethylene at temperature of 300 to 600 C. with an activated catalyst comprising tungsten, iron, and an alkali or alkaline earth metal or compounds thereof on silica gel carrier, and wherein the atomic ratio of iron to tungsten is from 1:20 to 2:1, to produce styrene, and continuing said contact until said catalyst has been at least partially deactivated by coke deposition, removing said deactivated catalyst from contact with reactants and regenerating said catalyst by oxidizing coke from said catalyst with an oxygen containing gas to produce an oxidized catalyst with reduced coke content and thereafter activating said catalyst by contacting said oxidized catalyst with activating gas at 400 to 600 C. for a time sufficient to activate said catalyst, and thereafter returning said catalyst to contact with stilbene and ethylene for further reverse disproportionation of stilbene and ethylene into styrene.

9. Process of claim 8 wherein the activating gas is carbon monoxide.

10. Process of claim 8 wherein the catalyst contains 0.1 to 10 Wt % W, 0.01 to 2 wt % alkali or alkaline earth component, and 0.005 to 5 wt % Fe.

11. Process of claim 8 wherein the catalyst contains 1 to 6 wt % W, as $WO_3$, 0.05 to 2 wt % Fe as $Fe_2O_3$ and 0.03 to 0.3 wt % K as $K_2O$.

12. Process of claim 8 wherein the atomic ratio of iron to tungsten is 1:5.

* * * * *